United States Patent [19]

Cassinelli et al.

[11] 4,276,289

[45] Jun. 30, 1981

[54] ANTITUMOR GLYCOSIDES, THEIR PREPARATION AND USE

[75] Inventors: Giuseppe Cassinelli, Voghera; Daniela Ruggieri, Milan; Federico Arcamone, Nerviano; Aurelio di Marco, Milan, all of Italy

[73] Assignee: Farmitalia Carlo Erba, S.p.A., Italy

[21] Appl. No.: 131,035

[22] Filed: Mar. 17, 1980

[30] Foreign Application Priority Data

Mar. 17, 1979 [GB] United Kingdom .............. 9462/79

[51] Int. Cl.$^3$ .................. A61K 31/70; C07H 15/24
[52] U.S. Cl. .................................. 424/180; 536/17 A
[58] Field of Search ................... 424/180; 536/17 A

[56] References Cited

U.S. PATENT DOCUMENTS

| | | | |
|---|---|---|---|
| 4,046,878 | 9/1977 | Patelli et al. | 536/17 A |
| 4,077,988 | 3/1978 | Arcamone et al. | 536/17 A |
| 4,107,423 | 8/1978 | Arcamone et al. | 536/17 A |
| 4,183,919 | 1/1980 | Cassinelle et al. | 536/17 A |

FOREIGN PATENT DOCUMENTS

2743675  4/1978  Fed. Rep. of Germany ........ 536/17 A

Primary Examiner—Johnnie R. Brown
Assistant Examiner—Blondel Hazel
Attorney, Agent, or Firm—Berger & Palmer

[57] ABSTRACT

Anthracycline glycosides of the formula I

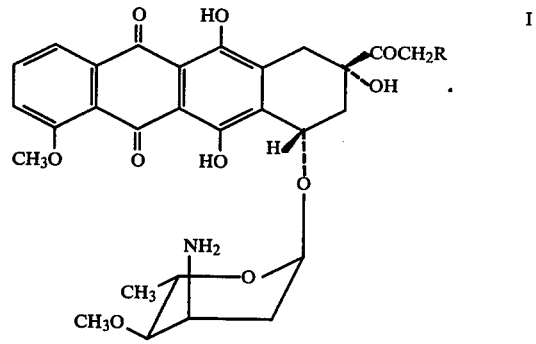

wherein R is hydrogen or hydroxyl and the hydrochlorides thereof, and which are useful in treating certain mammalian tumors, are prepared by condensing daunomycinone with the novel sugar, 4-O-methyl-2,3,6-trideoxy-3trifluoroacetamidoribohexopyranosyl chloride in an inert organic solvent and in the presence of a soluble silver salt and a dehydrating agent to form 3', 4'-diepi-4'-O-methyl-N-trifluoroacetyl daunorubicin, and removing the N-trifluoroacetyl group therefrom. This gives the compound wherein R is hydrogen. The former is converted to the corresponding hydroxyl compound by conventional means.

5 Claims, No Drawings

ANTITUMOR GLYCOSIDES, THEIR PREPARATION AND USE

CROSS REFERENCE TO RELATED APPLICATIONS

This application is related to and incorporates by reference the contents of U.S. Pat. Nos. 3,803,124; 4,112,076 and Belgian Pat. No. 862,102, granted on June 21, 1978, all of which are owned by the unrecorded assignee hereof.

BACKGROUND OF THE INVENTION

1. Field of the Invention

The present invention relates to anthracycline antitumor glycosides, methods for their preparation, compositions containing same and the use thereof as well as certain novel intermediates used in their preparation.

2. The Prior Art

Daunorubicin and doxorubicin are both well known anthracycline antitumor glycosides, and both their preparation and use are amply described in the prior art.

SUMMARY OF THE INVENTION

The present invention provides, in one aspect thereof, a new class of anthracycline glycoside antibiotics of the formula I

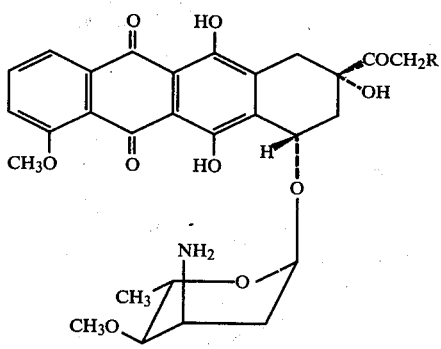

wherein R is hydrogen or hydroxyl and the hydrochlorides thereof. The compound wherein R is hydrogen is 3', 4'-diepi-4'-O-methyl-daunorubicin and the compound wherein R is hydroxyl is 3',4'-diepi-4'-O-methyl-doxorubicin.

These compounds are made by a method which is also within the scope of the invention, said method involving the use of a novel halosugar that is also part of the invention. Moreover, the process by which the halosugar is made is also within the scope of the invention.

Thus, in another aspect, the invention provides a method for the preparation of a 3',4'-diepi-4'-O-methyl-daunorubicin (I,R=H). According to the process, the known compound daunomycinone (which is the aglycone of daunorubicin) is condensed with 4-O-methyl-2,3,6-trideoxy-3-trifluoroacetamidoribohexopyranosyl chloride of the formula III

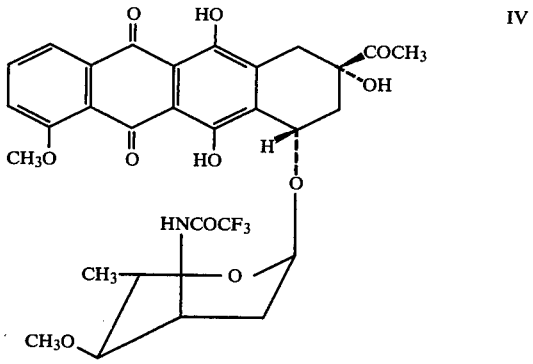

in an inert organic solvent in the presence of a soluble silver salt as a catalyst and a molecular sieve as a dehydrating agent to form the protected α-glycoside IV and removing the N-trifluoracetyl protecting group therefrom by mild alkaline hydrolysis. The 3',4'-diepi-4'-O-methyl-daunorubicin may then be isolated as its hydrochloride.

The inert organic solvent in which the condensation is carried out is preferably chloroform or methylene dichloride. The soluble silver salt is preferably silver trifluoromethanesulphonate, and the molecular sieve is preferably Merck molecular sieve. The conditions under which the condensation is carried out may be those described in U.S. Pat. No. 4,112,076, owned by the unrecorded assignee hereof.

The protected halo-sugar III is also a novel compound and is within the scope of the invention.

In yet another aspect, the invention provides the novel halosugar of formula III above.

In a still further aspect, the invention provides a process for preparing halosugar III, said process proceeding through several novel intermediates which are also part of the invention. According to this aspect of the invention, the protected halosugar III is prepared from the known compound methyl 2,3,6-trideoxy-3-trifluoracetamido-α-L-ribohexopyranoside of the formula V, which is described in U.S. Pat. No. 4,112,076, owned by the unrecorded assignee hereof

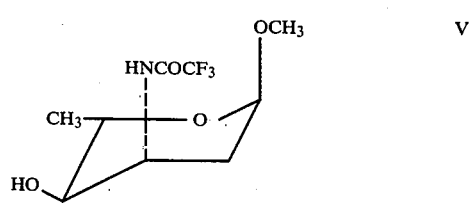

In accordance with the process, compound V is treated with diazomethane-boron trifluoride etherate reagent in methylene dichloride as described by J. O. Deferrari et al. (Methods in Carbohydrate Chemistry, Vol. VI, p. 365, 1972, Academic Press, New York and London) and in Belgian Pat. No. 862,102, granted on June 21, 1978, but at a lower temperature (−70° C.) than in the prior art methods, to give the previously unknown 4-O-methyl-derivative VI.

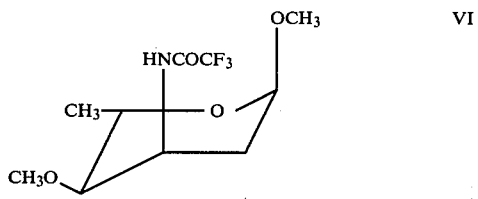

Acid hydrolysis of compound VI affords compound VII containing a free hydroxyl group in the 1-position.

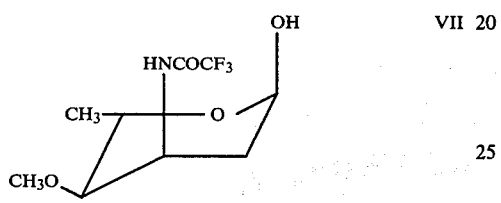

Compound VII is reacted with p-nitrobenzoyl chloride in anhydrous pyridine in order to obtain the corresponding 1-O-p-nitrobenzoyl derivative VIII.

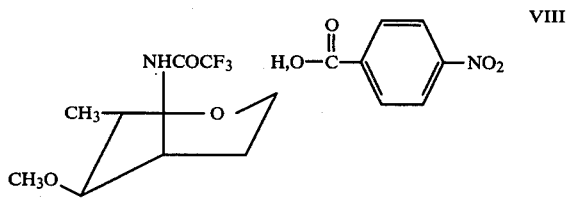

Finally, compound VIII is subjected to treatment with anhydrous hydrogen chloride in anhydrous methylene dichloride to give the 1-chloro derivative III. The intermediate compounds VI, VII and VIII are also part of the invention.

In order to obtain 3′,4′-diepi-4′O-methyl-doxorubicin (I,R=OH), 3′,4′-diepi-4′-O-methyl-daunorubicin (I,R=H) is brominated and the resultant 14-bromo derivative is hydrolyzed with aqueous sodium formate in accordance with the conditions described in U.S. Pat. No. 3,803,124 which is owned by the unrecorded assignee hereof. Finally, 3′,4′-diepi-4′-O-methyl-doxorubicin may be isolated as its hydrochloride.

In other aspects, the invention provides pharmaceutical compositions comprising a compound according to formula I in combination with an inert carrier therefor as well as methods of using said compounds in treating certain mammalian tumors, for example, P 388 leukemia.

DESCRIPTION OF THE PREFERRED EMBODIMENTS

The invention is illustrated in greater detail by the following examples wherein all parts given are by weight, unless otherwise specified.

EXAMPLE 1

Preparation of the halosugar: 4-O-methyl-2,3,6-trideoxy-3-trifluoracetamido-ribohexopyranosyl chloride (III).

A solution of 11.7 g; 45 mmol of methyl 2,3,6-trideoxy-3-trifluroacetamido-α-L-ribohexopyranoside (V) in 100 ml of anhydrous methylene dichloride was treated at −70° C. with 0.6 ml of boron trifluoride etherate. While maintaining the temperature at −70° C., an excess of diazomethane in anhydrous methylene dichloride was added until a faint yellow color persisted. After 60 minutes at −70° C., a white solid (polymethylene) which precipitated out, was removed by filtration. The filtrate was washed successively with a 10% sodium bicarbonate solution and water, and then dried over anhydrous sodium sulphate. The filtrate was then evaporated to leave a residue, which was then chromatographed on a silica gel column. Elution of the column with chloroform gave pure methyl 4-O-methyl-2,3,6-trideoxy-3-trifluoroacetamido-α-L-ribohexopyranoside (VI) as an amorphous solid; m.p. 55°–60° C; $[\alpha]_D^{23°} = -110°$ (c=0.5 in CHCl$_3$); mass spectrum: m/e 271 (M+). The p.m.r. spectrum showed absorption at: 1.30 (d, CH$_3$—C—5), 2.95 (dd, J=9.5 and 4.0 Hz, C—4—H), 3.42 and 3.43 (s,2 CH$_3$O—), 3.70 (dq, J=6.0 and 9.0 Hz, C—5—H), 4.45–4.85 (m, C—3—H) and 4.75 δ (broad s W$_H$=5.5 Hz, C—1—H).

To a solution of 1.76 g; 6.5 mmol of compound VI in 35 ml of acetic acid there were added 140 ml of water. The solution was then heated at 100° C. for 1 hour. The solvent was then evaporated off and the residue was recrystallized from carbon tetrachloride to give 1.64 g (yield 98%) of 4-O-methyl-2,3,6-trideoxy-3-trifluoroacetamido-α-L-ribohexopyranose (VII); m.p. 113°–115° C.; $[\alpha]_D^{23°} = -61.5°$ (c=0.5 in CHCl$_3$); mass spectrum; m/e 257 (M+). The p.m.r. spectrum showed absoption at: 1.27 (d, CH$_3$—C—5), 2.96 (dd, J=9.5 and 4.0 Hz, C—4—H), 3.44 (s, CH$_3$O), 4.00 (dq, J=6.5 and 9.5 Hz, C—5—H), 4,69 (m, C—3—H) and 5.32 (broad s, W$_H$=6.0 Hz, C—1—H).

A solution of 1.64 g; 6.38 mmol of compound VII in 76 ml of anhydrous pyridine was treated at 0° C. under stirring with 2 g of p-nitrobenzoyl chloride. After 30 minutes at 0° C. and then 20 hours at room temperature, the reaction mixture was poured into iced water and extracted with chloroform; the combined chloroform extracts were washed successively with a 10% potassium bisulphate solution, 10% sodium bicarbonate solution and finally with water, after which it was dried over anhydrous sodium sulphate and then concentrated to a residue. The residue was chromatographed on a silica gel column. Elution with a chloroform: acetone mixture (95:5 by volume) gave 1.76 g (yield 68%) of 4-O-methyl-1-O-p-nitrobenzoyl-2,3,6-trideoxy-3-trifluoroacetamido-L-ribohexopyranose (VIII).

A solution of 1.76 g; 4.34 mmol of compound VIII in 48 ml of anhydrous methylene dichloride was saturated at 0° C. with anhydrous hydrogen chloride. The resulting precipitate of p-nitrobenzoic acid was filtered off under anhydrous conditions and the filtrate was evaporated to give a residue of 1.2 g (yield 100%) of 4-O-methyl-2,3,6-trideoxy-3-trifluoroacetamido-L-ribohexopyranosyl chloride (III).

This material was suitable for use in the coupling reaction described in Example 2 without further purification.

EXAMPLE 2

3',4'-diepi-4'O-methyl-daunorubicin (I, R=H)

To a solution of 2.7 6.78 mmol of daunomycinone in 310 ml of anhydrous methylene dichloride there were added 1.2 g of 4-O-methyl-2,3,6-trideoxy-3-trifluoroacetamido-L-ribohexopyranosyl chloride (III) in 25 ml of anhydrous methylene dichloride) and 8.2 g of molecular sieve (4 Å Merck). The reaction mixture was then treated with 1.4 g of silver trifluoromethanesulphonate in 34 ml of anhydrous diethyl ether under vigorous stirring. After 1 hour at room temperature, the reaction mixture was neutralized with 0.72 ml of s-collidine, filtered, washed with 0.1 N aqueous hydrochloric acid and then with water, after which it was dried over anhydrous sodium sulphate and evaporated under vacuum. Chromatographic purification of the crude residue on a silica gel column, using chloroform; acetone (9:1 by volume) as the eluent gave 1.42 g (yield 51%) of 3',4'-diepi-4'-O-methyl-N-trifluoroacetyl-daunorubicin (IV); m.p. o4°–95° C.; $[\alpha]_D^{23} = +137.5°$ (c=0.05, in CHCl$_3$). The p.m.r. spectrum showed absorption at: 1.29 (d, CH$_3$—C—5'), 2.40 (s, CH$_3$CO), 2.97 (dq, J=9.0 and 4.0 Hz, C—4'—H), 3.40 (s, CH$_3$O—C—4), 4.04 (s, CH$_3$O—C—4), 4.47–4.91 (m, C—3'—H), 5.13 (broad s, W$_H$=8.0 Hz, O—7—H), 5.42 (broad s, W$_H$=6.0 Hz, C—1—H), 7.35 (dd, J=7.5 and 2.0 Hz, C—3—H), 7.33 (dd, J=7.5 Hz, C—2—H), 7.87 (dd, J=7.5 and 2.0 Hz, C—1—H), 13.40 and 14.20 δ (two s, C—6—OH and C—11—OH).

A solution of 1.4 g; 2.2 mmol of compound IV in 24 ml of acetone was treated with 57 ml of 0.2 N aqueous sodium hydroxide and stirred under nitrogen at room temperature. After 3 hours, the reaction mixture was adjusted to pH 4 and 1 N aqueous hydrochloric acid and then extracted wih chloroform in order to eliminate some impurities. The aqueous phase, after being adjusted to pH 7.5, was extracted with chloroform. The combined chloroform extracts were washed with distilled water, dried over anhydrous sodium sulphate, concentrated to a small volume and acidified to pH 4.5 with 0.5 N methanolic hydrogen chloride. The addition of diethyl ether to the thusly acidified solution gave a precipitate of 500 mg (yield 39%) of 3',4'-diepi-4'-O methyl-daunorubicin (I, R=H) as the hydrochloride m.p. 188°–192° C. (with decomposition); $[\alpha]_D^{23}=+373°$ (c=0.015 in methanol).

EXAMPLE 3

3',4'-diepi-4'-O-methyl-doxorubicin (I, R=OH)

A solution of 0.29 g; 0.5 mmol of 3', 4'-diepi-4'-O-methyl-daunorubicin hydrochloride in a mixture of anhydrous methanol (4 ml), dioxan (11.5 ml) and ethyl orthoformate (0.3 ml) was treated with 1.2 ml of a 1.3 M solution of bromine in chloroform. After 2 hours at 10° C. the reaction mixture was poured into 90 ml of a 2:1 (by volume) mixture of diethyl ether and n-hexane. The resulting precipitate, after being filered and washed with diethyl ether, was dissolved in 20 ml of a 1:1 (by volume) mixture of acetone and 0.25 N aqueous hydrobromic acid. After 20 hours at 30° C. there were added to the reaction mixture, 5 ml of a 1.3 N aqueous solution of sodium formate. The resulting mixture was stirred for 48 hours at 30° C., after which it was extracted with chloroform in order to remove some lipophilic impurities. The aqueous phase was then adjusted to pH 7.6 and repeatedly extracted with chloroform. The combined chloroform extracts were then dried over anhydrous sodium sulphate and evaporated to a small volume under vacuum. To the resulting solution after having been adjusted to pH 3.5 with anhydrous methanolic hydrogen chloride, diethyl ether was added to precipitate 3',4'diepi-4'-O-methyl-doxorubicin (I, R=OH) as the hydrochloride: m.p. 185°–187° C. (with decomposition): $[\alpha]_D^{23} = +188°$ (c=0.05 in methanol).

BIOLOGICAL ACTIVITY

The biological activity of the compounds according to the invention was tested in vitro against HeLa cells in comparison with daunorubicin and doxorubicin. The results of these tests are given in Table I.

TABLE I

| Compound | ID$_{50}$ on HeLa Cells (ng/ml) |
|---|---|
| Daunorubicin | 14 |
| 3',4'-diepi-4'-O-methyl daunorubicin | 36 |
| Doxorubicin | 9.5 |
| 3',4'-diepi-4'-O-methyl doxorubicin | 5.9 |

The compounds of the invention were also tested in vivo to demonstrate their activity against P 388 leukemia in comparison with daunorubicin and doxorubicin. These test data are given in Table II.

TABLE II

| | Activity against P 388 Leukemia (treatment i.p. on day 1 after tumor implantation) | | | |
|---|---|---|---|---|
| Compound | Dose mg/kg | T/C % | Toxicity | LTS* |
| Daunorubicin | 2.9 | 172,168 | 0/18 | 0/18 |
| | 4.4 | 181,187 | 0/18 | 0/18 |
| | 6.6 | 163 | 3/8 | 0/8 |
| 3',4'-diepi-4'-O-methyl daunorubicin | 6.6 | 145 | 0/8 | 0/8 |
| | 10 | 154 | 0/8 | 0/8 |
| | 15 | 190,213 | 0/18 | 0/18 |
| | 22 | 222 | 0/10 | 0/10 |
| | 33 | 231 | 2/10 | 1/10 |
| Doxorubicin | 4.4 | 209 | 0/8 | 2/10 |
| | 6.6 | 233 | 0/8 | 0/10 |
| 3',4'-diepi-4'-O-methyl doxorubicin | 1.9 | 180 | 0/10 | 0/10 |
| | 2.9 | 200 | 2/10 | 0/10 |
| | 4.4 | 109 | 10/10 | 0/10 |
| | 6.6 | 76 | 10/10 | 0/10 |

*LTS = long term survivors

Variations and modifications can, of course, be made, without departing from the spirit and scope of the invention.

Having thus described our invention what we desire to secure by Letters Patent and hereby claim is:

1. An anthracycline glycoside of the formula I:

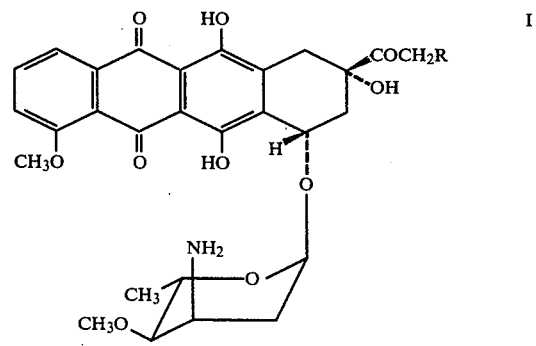

wherein R is hydrogen or hydroxyl and the hydrochlorides thereof.

2. A compound according to claim 1 wherein R is hydrogen.

3. A compound according to claim 1 wherein R is hydroxyl.

4. A pharmaceutical composition for inhibiting the growth of P 388 leukemia comprising a therapeutically effective amount of an anthracycline glycoside as claimed in claim 1 in combination with an inert carrier therefor.

5. A method of inhibiting the growth of P 388 leukemia comprising intraperitoneally administering to a host afflicted therewith, a therapeutically effective amoung of an anthracycline glycoside as claimed in claim 1.

* * * * *